United States Patent
Liao et al.

(10) Patent No.: US 10,081,554 B2
(45) Date of Patent: Sep. 25, 2018

(54) USE OF AMINO-CONTAINING NEUTRAL PHOSPHINE EXTRACTANT IN EXTRACTION AND SEPARATION OF THORIUM AND PROCESS OF USING SAME

(71) Applicant: CHANGCHUN INSTITUTE OF APPLIED CHEMISTRY, CHINESE ACADEMY OF SCIENCES, Jilin (CN)

(72) Inventors: Wuping Liao, Jilin (CN); Yanling Li, Jilin (CN); Zhifeng Zhang, Jilin (CN); Guolong Wu, Jilin (CN); Youcai Lu, Jilin (CN)

(73) Assignee: Changchun Institute Of Applied Chemistry, Chinese Academy Of Sciences, Jilin (CN)

( * ) Notice: Subject to any disclaimer, the term of this patent is extended or adjusted under 35 U.S.C. 154(b) by 0 days.

(21) Appl. No.: 15/329,176

(22) PCT Filed: Apr. 22, 2015

(86) PCT No.: PCT/CN2015/077208
§ 371 (c)(1),
(2) Date: Jan. 25, 2017

(87) PCT Pub. No.: WO2016/090808
PCT Pub. Date: Jun. 16, 2016

(65) Prior Publication Data
US 2017/0267540 A1      Sep. 21, 2017

(30) Foreign Application Priority Data
Dec. 11, 2014  (CN) .......................... 2014 1 0765062

(51) Int. Cl.
| | | |
|---|---|---|
| *C01F 15/00* | (2006.01) | |
| *C01F 1/00* | (2006.01) | |
| *C07F 9/40* | (2006.01) | |
| *C22B 3/06* | (2006.01) | |
| *C22B 60/02* | (2006.01) | |
| *C22B 3/38* | (2006.01) | |

(52) U.S. Cl.
CPC .............. *C01F 15/00* (2013.01); *C01F 1/00* (2013.01); *C07F 9/4006* (2013.01); *C07F 9/4009* (2013.01); *C22B 3/0059* (2013.01); *C22B 3/065* (2013.01); *C22B 60/0291* (2013.01); *C01P 2006/80* (2013.01); *Y02P 10/234* (2015.11)

(58) Field of Classification Search
CPC .......... C01F 15/00; C01F 1/00; C07F 9/4009; C22B 60/0291; C22B 3/065
USPC ....................................................... 423/6–10
See application file for complete search history.

(56) References Cited

U.S. PATENT DOCUMENTS

| | | |
|---|---|---|
| 2,635,112 A | 4/1953 | Fields |
| 2014/0170039 A1* | 6/2014 | Li .......................... C22B 60/291 423/10 |

FOREIGN PATENT DOCUMENTS

| | | |
|---|---|---|
| CN | 1254024 A | 5/2000 |
| CN | 1394971 A | 2/2003 |
| CN | 1721559 A | 1/2006 |
| CN | 102316963 A | 1/2012 |
| CN | 102417992 A1 | 4/2012 |
| CN | 102994781 A | 3/2013 |
| CN | 103773954 A | 5/2014 |
| CN | 104131164 A | 11/2014 |

OTHER PUBLICATIONS

Laurent Germanaud et al., "Syntheses de phosphobetaines amphiphiles neutres a distances intercharge variables," Bulletin De La Societe Chimique De France, 1988, No. 4, pp. 699-703.

* cited by examiner

*Primary Examiner* — Steven J Bos
(74) *Attorney, Agent, or Firm* — Baker & Hostetler LLP

(57) ABSTRACT

The present invention relates to use of an amino-containing neutral phosphine extractant of Formula I in extraction and separation of thorium, and a process of extracting and separating thorium using the amino-containing neutral phosphine extractant of Formula I,

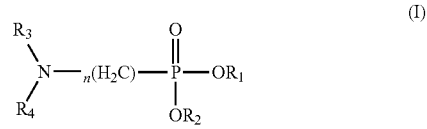

wherein, $R_1$ and $R_2$ are each independently selected from the group consisting of $C_1$-$C_{12}$ alkyl, $R_3$ and $R_4$ are each independently selected from the group consisting of $C_{1\text{-}16}$ alkyl and hydrogen, and n is an integer of 1 to 8.

19 Claims, No Drawings

USE OF AMINO-CONTAINING NEUTRAL PHOSPHINE EXTRACTANT IN EXTRACTION AND SEPARATION OF THORIUM AND PROCESS OF USING SAME

CROSS-REFERENCE TO RELATED APPLICATIONS

This application is a National Stage of International patent application PCT/CN2015/077208, filed on Apr. 22, 2015, which claims priority to Chinese patent application No. CN 201410765062.1, filed on Dec. 11, 2014, the disclosures of which are incorporated by reference in their entirety.

TECHNICAL FIELD

The present invention relates to a process of extracting and separating thorium, and particularly, to use of an amino-containing neutral phosphine extractant in extraction and separation of thorium and a process of extracting and separating thorium by using the amino-containing neutral phosphine extractant.

BACKGROUND ART

Thorium, which is an actinide element, is usually accompanied with rare earth elements. Tributylphosphate (TBP) was used as an extractant to extract and separate thorium from nitrate medium in the early process of separating thorium. However, TBP is consumed in large amount due to the high water solubility thereof. In addition, the extraction process should be performed in a medium containing a high concentration of nitric acid, which causes consumption of a large amount of nitric acid and accelerates the decomposition of TBP.

Currently, N1923, which is a primary amine, is predominantly used to extract and separate thorium from a sulfate medium, while di(2-ethylhexyl)-2-ethylhexylphosphonate (DEHEHP) and the like may be used to extract and separate thorium from a nitric acid system. For example, Chinese patents ZL98122348.6 and ZL02123913.4 disclose processes of extracting and separating thorium from the leaching of bastnaesite, or mixed bastnaesite-monazite ore, in which the primary amine N1923 is used as the extractant to extract and separate thorium, and thorium in the leaching may be recovered and enriched with a purity of 95%~99% and a recovery of 95%. In addition, acidic phosphorus (phosphine) extractants, such as P204 and P507, have good extractive performance for thorium, but the stripping of the loaded thorium is hard so that these acidic extractants are rarely applied in industries.

The present inventors have been studying the separation and purification of thorium and rare earth elements for a long term, and were granted two Chinese invention patents, ZL201110074345.8 and ZL201210552752.X, in the separation and purification of thorium. The extractants used in these two patents are both a neutral phosphine extractant with a formula of $G_3P=O$, wherein each G is independently selected from the group consisting of alkyl and alkoxy. However, there are still some disadvantages such as non-easily obtained raw material, high cost and limit to use in a special medium.

Thus, there is a need to develop novel processes of extracting and separating thorium, and search for novel extraction systems.

SUMMARY OF THE INVENTION

To address above problems, one object of present invention is to provide the use of an amino-containing neutral phosphine extractant in extraction and separation of thorium. Another object of present invention is to provide a process of extracting and separating thorium using the amino-containing neutral phosphine extractant.

In an aspect of present invention, provided is use of an amino-containing neutral phosphine extractant of the following Formula I in extraction and separation of thorium, $$\begin{array}{c} R_3 \\ \diagdown \\ N-{}_n(H_2C)-\overset{\displaystyle O}{\underset{\displaystyle |}{\overset{\displaystyle \|}{P}}}-OR_1 \\ \diagup \\ R_4 \quad\quad\quad OR_2 \end{array} \quad (I)$$

wherein, $R_1$ and $R_2$ are each independently selected from the group consisting of $C_1$-$C_{12}$ alkyl, $R_3$ and $R_4$ are each independently selected from the group consisting of $C_1$-$C_{16}$ alkyl and hydrogen, and n is an integer of 1 to 8.

In another aspect of present invention, provided is a process of extracting and separating thorium, comprising a step of extracting and separating thorium using the amino-containing neutral phosphine extractant of Formula I.

The process of extracting and separating thorium according to present invention may be performed by solvent extraction, for example, by diluting the amino-containing neutral phosphine extractant of present invention into a liquid extraction system, or solid-liquid extraction, for example, by introducing the amino-containing neutral phosphine extractant of present invention into a solid separation material, such as an extraction resin, etc.

Advantageous Effect

The amino-containing neutral phosphine extractant used in present invention is suitable to various mineral acid media, has high extraction ability toward thorium, easy back-extraction, a simple synthetic method with easily obtained raw materials and low synthetic cost, and thus has a high industrial application value.

DETAILED DESCRIPTION

The present invention will be described in detail below, but is not limited thereto.

In an aspect of present invention, provided is use of an amino-containing neutral phosphine extractant of formula I in extraction and separation of thorium, $$\begin{array}{c} R_3 \\ \diagdown \\ N-{}_n(H_2C)-\overset{\displaystyle O}{\underset{\displaystyle |}{\overset{\displaystyle \|}{P}}}-OR_1 \\ \diagup \\ R_4 \quad\quad\quad OR_2 \end{array} \quad (I)$$

wherein, $R_1$ and $R_2$ are each independently selected from the group consisting of $C_1$-$C_{12}$ alkyl, preferably $C_4$-$C_{10}$ alkyl, more preferably $C_5$-$C_9$ alkyl, and most preferably $C_6$-$C_8$ alkyl;

$R_3$ and $R_4$ are each independently selected from the group consisting of $C_1$-$C_{16}$ alkyl and hydrogen, and n is an integer of 1 to 8, preferably an integer of 1 to 4, and more preferably 1 or 2.

In the Formula I, $R_1$ and $R_2$ are the same or different. Preferably, the sum of carbon atoms of $R_1$ and $R_2$ is an integer of 8 to 20, preferably 10 to 18. In addition, $R_1$ and $R_2$ are preferably the same alkyl, more preferably $C_5$-$C_9$ alkyl.

$R_3$ and $R_4$ are the same or different. Preferably, $R_3$ is selected from the group consisting of hydrogen and $C_1$-$C_{10}$ alkyl, preferably C1-$C_8$ alkyl and hydrogen, $R_4$ is selected from the group consisting of $C_1$-$C_{14}$ alkyl, preferably $C_1$-$C_{12}$ alkyl. Preferably, the sum of carbon atoms of $R_3$ and $R_4$ is an integer of 1 to 16, preferably 2 to 13.

Preferably, in the amino-containing phosphine neutral extractant of Formula I of the present invention, the sum of carbon atoms of $R_1$, $R_2$, $R_3$, $R_4$ and —$(CH_2)_n$— is 14 to 36, including, but not limited to, 14, 15, 16, 17, 18, 19, 20, 21, 22, 23, 24, 25, 26, 27, 28, 29, 30, 31, 32, 33, 34, 35 and 36, preferably 16 to 34, and more preferably 18 to 33.

Preferably, the amino-containing neutral phosphine extractant of Formula I is one or more selected from the group consisting of di(2-ethylhexyl)-(2-ethylhexyl)aminomethylphosphonate, di(2-ethylhexyl) hexylaminomethylphosphonate, di(2-ethylhexyl) (N,N-diisobutylamino)methylphosphonate, di(2-ethylhexyl) butylaminomethylphosphonate, dihexyl dodecylaminomethylphosphonate.

The amino-containing neutral phosphine extractant of Formula I may be a commercially available product, or synthesized according to a process known in prior art, for example, *Bulletin De La Societe Chimique De France*, 1988, N4, p 699-703, etc.

For example, the amino-containing neutral phosphine extractant of Formula I may be synthesized as shown in Scheme 1, Scheme 1

$$R_3\text{NH}/R_4 + \text{Br}—(CH_2)_n—\underset{OR_2}{\underset{|}{P}}(=O)—OR_1 \longrightarrow$$

II     III $$R_3/R_4\text{N}—(CH_2)_n—\underset{OR_2}{\underset{|}{P}}(=O)—OR_1$$

I wherein, Compound II and III are subjected to a substitution reaction to form the amino-containing neutral phosphine extractant of Formula I, wherein, $R_1$, $R_2$, $R_3$, $R_4$ and n are defined the same as those in Formula I.

The compound III may be a commercially available product, or synthesized according to a process known in prior art. For example, compound III may be synthesized below as shown in Scheme 2, Scheme 2

$$R_5O—\underset{OR_2}{\underset{|}{P}}(=O)—OR_1 + \text{Br}—(CH_2)_n—\text{Br} \longrightarrow$$

IV     V $$\text{Br}—(CH_2)_n—\underset{OR_2}{\underset{|}{P}}(=O)—OR_1$$

III wherein Compound IV and V are subjected to a substitution reaction to form compound III, wherein, $R_1$, $R_2$ and n are defined the same as those in Formula I.

$R_5$ is selected from the group consisting of $C_1$-$C_{12}$ alkyl, preferably $C_4$-$C_{10}$ alkyl, preferably $C_5$-$C_9$ alkyl, and most preferably $C_6$-$C_8$ alkyl.

The compound IV may be a commercially available product, or synthesized according to a process known in prior art.

Alternatively, the amino-containing neutral phosphine extractant of Formula I may be synthesized below as shown in Scheme 3, Scheme 3

$$R_3\text{NH}/R_4 + CH_2O + H—\underset{OR_2}{\underset{|}{P}}(=O)—OR_1 \longrightarrow$$

II     VI $$R_3/R_4\text{N}—(CH_2)_n—\underset{OR_2}{\underset{|}{P}}(=O)—OR_1$$

wherein, Compound II and VI and formaldehyde are subjected to a condensation reaction to form the amino-containing neutral phosphine extractant of formula I, wherein, $R_1$, $R_2$, $R_3$, and $R_4$ are defined the same as those in Formula I, and n is 1.

The formaldehyde may be free formaldehyde or paraformaldehyde. The compound IV may be a commercially available product, or synthesized according to a process known in prior art.

In another aspect of present invention, provided is a process of extracting and separating thorium, comprising a step of extracting and separating thorium using the amino-containing neutral phosphine extractant of Formula I.

In one embodiment, the process of extracting and separating thorium of present invention may be performed by solvent extraction comprising: mixing a neutral phosphine extraction system (hereinafter sometimes referred to as organic phase) containing the amino-containing neutral phosphine extractant of Formula I and a thorium-containing feed solution to perform extraction to give a thorium-loaded organic phase and a raffinate.

The neutral phosphine extraction system contacts with thorium in the feed solution to form a thorium chelate so as to extract thorium into the organic phase from the feed solution.

The neutral phosphine extraction system includes the amino-containing neutral phosphine extractant of Formula I, an optional auxiliary extractant, an optional phase modifier and a diluent. Preferably, the neutral phosphine extraction system is consisted of the above components.

Preferably, the above components have the volume ratio of the amino-containing neutral phosphine extractant:the auxiliary extractant:the phase modifier:the diluent=about 1-60:about 0-40:about 0-20:about 40-110, more preferably, the amino-containing neutral phosphine extractant:the auxiliary extractant:the phase modifier:the diluent=about 3-40: about 0-20:about 0-20:about 50-100; and even more preferably, the amino-containing neutral phosphine extractant: the auxiliary extractant:the phase modifier:the diluent=about 3-30:about 0-15:about 0-15:about 60-99; for example, the amino-containing neutral phosphine extractant:the auxiliary extractant:the phase modifier:the diluent=about 3-30:about 3-15:0:about 60-99, or the amino-containing neutral phosphine extractant:the auxiliary extractant:the phase modifier: the diluent=about 3-30:0:about 5-15:about 60-99; or the amino-containing neutral phosphine extractant:the auxiliary extractant:the phase modifier:the diluent=about 3-30:0:0: about 60-99.

The auxiliary extractant may be selected from the group consisting of phosphorus (phosphine) extractant of Formula VII:

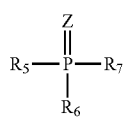

(VII)

wherein,

Z is O or S;

$R_5$ is selected from the group consisting of hydrogen, $C_1$-$C_{12}$ alkyl, $C_1$-$C_{12}$ alkoxy, —SH, and —$NH_2$ substituted by at least one substituent selected from the group consisting of $C_1$-$C_{12}$ alkyl; preferably hydrogen, $C_1$-$C_{10}$ alkyl, $C_1$-$C_{10}$ alkoxy, —SH, and —$NH_2$ substituted by at least one substituent selected from the group consisting of $C_4$-$C_{10}$ alkyl; and more preferably $C_1$-$C_{10}$ alkyl and $C_1$-$C_{10}$ alkoxy;

$R_6$ and $R_7$ are each independently selected from the group consisting of $C_4$-$C_{12}$ alkyl, $C_4$-$C_{12}$ alkoxy, and —$NH_2$ substituted by at least one substituent selected from the group consisting of $C_4$-$C_{12}$ alkyl; preferably $C_4$-$C_{10}$ alkyl, $C_4$-$C_{10}$ alkoxy, and —$NH_2$ substituted by at least one substituent selected from the group consisting of $C_4$-$C_{10}$ alkyl; and more preferably $C_4$-$C_{10}$ alkyl and $C_4$-$C_{10}$ alkoxy.

Suitable auxiliary extractant may be, a neutral phosphine extractant, such as tri(linear alkyl)phosphine oxide (Cyanex 923), tri(branched alkyl)phosphine oxide (Cyanex 925), trioctylphosphine oxide (TOPO), di(methylheptyl) methylphosphonate (P350), di(2-ethylhexyl)-2-ethylhexylphosphonate, tributyl-phosphate (TBP); an acidic phosphorus (phosphine) extractant, such as bis(2,4,4-trimethylpentyl) dithiophosphinic acid (Cyanex 301), di(2,4,4-trimethylpentyl)thiophosphinic acid (Cyanex 302), di(2-ethylhexyl)phosphoric acid (P204), mono-(2-ethylhexyl) 2-ethylhexylphosphonate (P507), bis(2,4,4-trimethylpentyl) phosphinic acid (Cyanex 272), and bis(2-ethylhexyl)phosphonic acid (P227 or P229); a neutral phosphamide extractant, for example, those disclosed in CN201410409451.0 and CN201410040023.5, such as triisooctylphosphamide, diisooctyl-isooctoxyphosphamide, isooctyl-diisooctoxyphosphamide, tri(diisobutyl)phosphoramide, bis(diisobutyl)-isooctoxyphosphamide, tridecylphosphamide, dihexyl-decyloxyphosphamide, etc.; or a mixed extractant thereof in any ratio.

Preferably, the auxiliary extractant is selected from the group consisting of tri(linear alkyl)phosphine oxide (Cyanex 923), tri(branched alkyl)phosphine oxide (Cyanex 925), trioctylphosphine oxide (TOPO), di(methylheptyl) methylphosphonate (P350), di(2-ethylhexyl) 2-ethylhexylphosphonate, tributyl phosphate (TBP) or a mixed extractant thereof in any ratio.

The phase modifier is one or more selected from the group consisting of $C_4$-$C_{10}$ alkanol; preferably one or more selected from the group consisting of n-octanol, isooctanol, 2-methyl heptanol or a mixed alcohol thereof in any ratio; and most preferably, the mixed alcohol or 2-methyl heptanol.

The diluent is selected from the group consisting of $C_5$-$C_{16}$ alkane, such as pentane, hexane, heptane, octane, nonane, decane, undecane, dodecane, tridecane, tetradecane, pentadecane, hexadecane, etc.; aviation kerosene; sulfonated kerosene; liquid paraffin; $C_5$-$C_{16}$ alicyclic hydrocarbon, such as cyclopentane, cyclopentane substituted by $C_1$-$C_4$ alkyl, cyclohexane, cyclohexane substituted by $C_1$-$C_4$ alkyl, decalin, etc.; $C_6$-$C_{10}$ aromatic hydrocarbon, such as benzene, toluene, xylene (including o-, m- and p-xylene and mixed xylene), etc. Preferably, the diluent is one or more selected from the group consisting of aviation kerosene, sulfonated kerosene, heptane and xylene.

The feed solution comprises thorium, a mineral acid and other non-thorium elements. In the feed solution, the concentration of thorium may be about 0.0001 to 2.0 mol/L, preferably 0.0003 to 1 mol/L. The acidity of the feed solution, expressed in molar concentration of hydrogen ion, may be 0.2 to 8 mol/L. Preferably, the feed solution is about 0.2 to 4 mol/L of a nitric acid, sulfuric acid or hydrochloric acid solution, more preferably about 1 to 3 mol/L of a nitric acid solution. In addition, the feed solution may further contain other elements, such as rare earths, alkali metal, alkali earth metal, transitional metal and non-metallic elements.

There is no limit for the raw material for preparing the feed solution, as long as the raw material contains thorium. The raw material suitable for preparing the feed solution includes various thorium-containing raw materials, such as monazite, bastnaesite, bastnaesite-monazite ore, a thorium enriched material, etc. The above thorium-containing raw material is pretreated, and dissolved in nitric acid, hydrochloric acid, sulfuric acid, phosphoric acid or a mixed acid thereof to prepare the feed solution suitable for present invention.

In addition, in practice, the feed solution may further contain other elements including rare earth, alkali metal, alkali earth metal, transition metal and non-metallic elements, and the kinds and contents thereof depend on the composition of the thorium-containing raw material ore. In this case, thorium may be selectively extracted and separated using the process of present invention, so as to be separated from non-thorium elements.

In addition, in the case that cerium(IV) is contained in the feed solution, the cerium(IV) and thorium may be extracted and separated in sequence, or the extraction and separation of thorium may be performed after cerium(IV) is reduced to cerium(III).

In the extraction step, the number of extraction stages may be 1 to 10, preferably 2 to 6. In addition, the flow ratio of the amino-containing neutral phosphine extraction system and the feed solution may be about 0.1-20:1, preferably about 0.1-10:1.

The process of present invention may further comprise an optional step of washing the thorium-loaded organic phase using a scrubbing solution, which may also be referred to as washing solution, washing acid or washing agent.

The scrubbing solution may be a solution of nitric acid, sulfuric acid or hydrochloric acid, or a mixture thereof in any ratio. The acidity of the scrubbing solution expressed by molar concentration of hydrogen ion may be 0.2 to 8 mol/L. The number of scrubbing stages may be 0 to 10, preferably 1 to 5. The flow ratio of the thorium-loaded organic phase and the scrubbing solution may be about 1:about 0.1-2, preferably about 1:about 0.2-1.

The process according to present invention further comprises a step of back-extracting the thorium-loaded organic phase using a stripping agent, which may also be referred to as stripping solution, back-extracting solution, back-extracting liquid, etc., to give a thorium-containing stripping solution. The stripping agent may be a solution of nitric acid, hydrochloric acid or sulfuric acid, or a mixture thereof, or a carbonate aqueous solution. The carbonate may be a salt of an alkali metal, an alkaline earth metal or an ammonium, e.g. a sodium salt, a potassium salt, etc. Preferably, in the case of using an acid solution as the back-extracting solution, the acidity expressed by molar concentration of the hydrogen ion is about 0.05 to 2 mol/L; in the case of using a sodium carbonate aqueous solution, its concentration may be about 0.5 to 5 wt %. Preferably, the back-extracting solution is a diluted nitric acid solution with a concentration of about 0.1 to 0.5 mol/L, or a sodium carbonate aqueous solution with a concentration of 0.5 to 3 wt %.

The number of back-extracting stages may be 1 to 10, preferably 1 to 6. In addition, the flow ratio of the thorium-containing extract and the back-extracting solution may be 1:0.1-10, preferably 1:0.1-2, more preferably 1:0.2-1.5.

In the solvent extraction of present invention, extracting, washing and back-extracting may be performed in a solvent extraction device known in the art, preferably in a series of separatory funnels, mixer-settler extractors or centrifugal extractors, and more preferably be performed in mixer-settler extractors or centrifugal extractors.

In the solvent extraction of present invention, the above extracting, washing and back-extracting may be performed in batches or continuously, preferably continuously.

In another embodiment, the process of extracting and separating thorium of present invention may be performed by solid-liquid extraction comprising extracting and separating thorium by using a solid separation material of the amino-containing neutral phosphine extractant of Formula I. More particularly, the process comprises contacting a solid separation material of the neutral phosphine extractant of Formula I with a thorium-containing feed solution, and performing extraction to give a thorium-containing solid separation material and a raffinate.

In one embodiment, the solid-liquid extraction is performed in a resin column, wherein the solid separation material is introduced into the resin column, and then the thorium-containing feed solution is introduced so that the solid separation material contacts with the thorium-containing feed solution to perform solid-liquid extraction.

The content of thorium in the raffinate is not particularly limited, but preferably not more than 0.02 g/l, more preferably not more than 0.01 g/l.

The description for the feed solution in solvent extraction is also applicable to the solid-liquid extraction, and will not be repeated here.

The solid separation material may be a resin, porous silica beads, diatomaceous earth, or the like, to support the neutral phosphine extractant of Formula I. Preferably, the solid separation material may be prepared by a conventional process in the art, for example, by loading the neutral phosphine extractant of Formula I on a resin, porous silica beads, or diatomaceous earth through dipping, in situ polymerization, chemical bonding, preferably by dipping, in situ polymerization or the like.

In a preferred embodiment, the solid separation material may be an extracting resin. The preparation process of the extracting resin is not particularly limited, as long as the extracting resin supports amino-containing neutral phosphine extractant of Formula I. For example, the extracting resin may be prepared by firstly preparing resin particles through dispersion polymerization, emulsion polymerization, bulk polymerization, suspension polymerization or the like, and then supporting the neutral phosphine extractant of Formula I on the resin particles, or by adding the neutral phosphine extractant of Formula I before or during polymerization, and then performing in situ polymerization.

In one embodiment, the extracting resin may be prepared by dispersion polymerization of the neutral phosphine extractant of Formula I, a styrene monomer and a divinyl-benzene monomer. For example, the extracting resin may be prepared by preparing an oil phase by mixing the neutral phosphine extractant of Formula I, a styrene monomer and a divinyl-benzene monomer and adding 2 wt % of an initiator relative to the total weight of the oil phase; preparing an aqueous phase by mixing deionized water having a volume of 10 times of the oil phase, 3 wt % of gelatin and 0.5 wt % of ammonium thiocyanate relative to the total weight of the aqueous phase; heating the aqueous phase at 50° C., slowly adding the oil phase after the gelatin is completely dissolved, keeping for half an hour, heating to 80° C. to polymerize for 5 h; and then heating to 90° C. to cure for half an hour, taking out the resin, washing, screening and air drying. The styrene monomer may be styrene, methylstyrene, ethylstyrene, etc.

In another embodiment, the solid separation material may be porous silica beads, diatomaceous earth, or the like, loading the neutral phosphine extractant of Formula I. The process of loading the neutral phosphine extractant of Formula I on the porous silica beads, diatomaceous earth, or the like is not particularly limited, as long as it is capable to support the neutral phosphine extractant of Formula I on the porous silica beads, or diatomaceous earth. For example, the solid separation material may be prepared by dissolving the neutral phosphine extractant of Formula I in a diluent, for example, an inert volatile solvent such as dichloromethane, chloroform, benzene, toluene, etc; adding the separation material such as porous silica beads, diatomaceous earth, or the like; slowly volatilizing the diluent under agitating.

In one embodiment, the solid-liquid extraction of present invention may further comprise an optional step of washing the thorium-loaded solid separation material using a scrubbing solution. The washing may further lower the content of impurities in the thorium-loaded solid separation material, so as to improve the purity of the final thorium product.

The description for the scrubbing solution in the above solvent extraction is also applicable to the solid-liquid extraction, and will not be repeated here.

The scrubbing solution after washing is collected. When the thorium content in the scrubbing solution is less than 0.1 g/L, the addition of scrubbing solution is stopped.

In one embodiment, the solid-liquid extraction further comprises a step of back-extracting the thorium-loaded solid separation material using a back-extracting solution. The back-extracting solution after back-extraction is collected.

When the thorium content in the back-extracting solution is less than 0.01 g/L, the addition of the back-extracting solution is stopped. The back-extracted solid separation material may be recycled to be used again to extract and separate thorium from a thorium-containing feed solution.

The description for the back-extracting solution in solvent extraction is also applicable to the solid-liquid extraction, and will not be repeated here.

As an example, the solid-liquid extraction may be performed as follows. A solid separation material is added into a resin column, and then the feed solution is added through an inlet to perform solid-liquid extraction. The raffinate is collected from an outlet, and the thorium content in the raffinate is measured regularly. The addition of the feed solution is stopped when the thorium content in the raffinate reaches 0.01 g/L. Optionally, washing is performed using a scrubbing solution. The scrubbing solution is collected and the addition of the scrubbing solution is stopped when the thorium content in the scrubbing solution is less than 0.1 g/L. Finally, the extracted thorium in the solid separation material is back-extracted by adding a back-extracting solution. The back-extracting solution is collected and the addition of the back-extracting solution is stopped when the thorium content in the back-extracting solution is less than 0.01 g/L.

The raffinate, if necessary, may be further treated according to a process known in the art to further extract rare earth elements or other valuable elements therein. For example, the rare earth elements in the raffinate may be converted into rare earth chloride or rare earth nitrate by extraction, or may be precipitated by alkali or double-salt precipitation to be used in the subsequent process.

The term "$C_1$-$C_{16}$ alkyl" used in present invention refers to a linear or branched alkyl having 1 to 16 carbon atoms, e.g., a linear or branched alkyl having 1, 2, 3, 4, 5, 6, 7, 8, 9, 10, 11, 12, 13, 14, 15 or 16 carbon atoms, including, but not limited to, methyl, ethyl, n-propyl, isopropyl, n-butyl, tert-butyl butyl, isobutyl, n-pentyl, neopentyl, isopentyl, hexyl, heptyl, octyl, nonyl, decyl, undecyl, dodecyl, tridecyl, tetradecyl group, pentadecyl, hexadecyl, etc. By such analog, $C_1$-$C_{10}$ alkyl, $C_4$-$C_{12}$ alkyl, $C_4$-$C_{10}$ alkyl, $C_5$-$C_9$ alkyl, and $C_6$-$C_8$ alkyl have similar meanings.

The term "$C_1$-$C_{12}$ alkoxy" used in present invention refers to a linear or branched alkoxy having 1-12 carbon atoms, for example, a linear or branched alkoxy having 1, 2, 3, 4, 5, 6, 7, 8, 9, 10, 11 or 12 carbon atoms, including, but not limited to, methoxy, ethoxy, n-propoxy, isopropoxy, n-butoxy, tert-butoxy, iso-butoxy, n-pentyloxy, neo-pentyloxy, iso-pentyloxy, hexyloxy, heptyloxy, octyloxy, nonyloxy, decyloxy, undecyloxy, dodecyloxy, etc. By such analog, $C_1$-$C_{10}$ alkoxy and $C_4$-$C_{10}$ alkoxy have similar meanings.

The term "$C_4$-$C_{10}$ alkanol" used in present invention refers to a linear or branched alkanol having 4-10 carbon atoms, for example, a linear or branched alkanol having 4, 5, 6, 7, 8, 9 or 10 carbon atoms, including, but not limit to, n-butanol, t-butanol, isobutanol, amyl alcohol, neopentyl alcohol, amyl alcohol, hexanol, heptanol, octanol, nonanol, decanol, etc.

The term "$C_5$-$C_{16}$ alkane" refers to a linear or branched alkane having 5 to 16 carbon atoms, for example, a linear or branched alkane having 5, 6, 7, 8, 9, 10, 11, 12, 13, 14, 15, 16 carbon atoms, such as pentane, hexane, heptane, octane, nonane, decane, undecane, dodecane, tridecane, tetradecane, pentadecane, hexadecane, etc.

The term "$C_5$-$C_{16}$ alicyclic hydrocarbon" refers to a saturated cyclic hydrocarbon having 5 to 16 carbon atoms including the carbon atom of the substituent thereof. The saturated cyclic hydrocarbon may be a monocyclic or bicyclic hydrocarbon, such as cyclopentane, cyclohexane, cycloheptane, cyclooctane, cyclononane, cyclodecane, decalin, etc, and the said substituent may be one or more selected from the group consisting of $C_1$-$C_4$ alkyl.

The term "$C_6$-$C_{10}$ aromatic hydrocarbon" refers to an aromatic hydrocarbon having 6 to 10 carbon atoms including carbon atoms of the substituent thereof, such as benzene and benzene substituted by one or more substituents selected from the group consisting of $C_1$-$C_4$ alkyl, for example, benzene, toluene, xylene, etc.

Unless otherwise stated, the numerical range listed in present invention includes endpoints, all point values obtained by increasing or decreasing by a minimum unit within the two endpoints, and all subsets consisted of the point values.

EXAMPLES

In order to further illustrate the present invention, provided are specific examples of present invention to help those skilled in the art to understand and practice the invention, but the present invention is not limited thereto.

Reagents and Sources

Di(ethylhexyl)phosphorite, di(n-octyl)phosphorite, di(n-heptyl)phosphorite, di(isooctyl)phosphorite, aviation kerosene and TBP were purchased from Shanghai Rare-earth Chemical Co. LTD.

Paraformaldehyde, di(n-hexyl)amine, diisobutylamine, n-butylamine, diisooctylamine, laurylamine, isooctylamine, dimethylamine, toluene, xylene, p-methylbenzenesulfonic acid and heptane were purchased from Aladdin Reagent.

Cyanex 923 and 2-methyl heptanol were purchased from Cytec Industries (Shanghai) Co. Ltd.

The feed solution, the scrubbing solution and the stripping agent were self-prepared in lab.

Other reagents (such as acids etc.) were commercially available analytical grade reagents.

The purity of the product was determined on an ICP-OES (Mode: Optical-8000, manufacturer: Perkin Elmer).

Nuclear magnetic resonance spectrometer was Varian Mercury 300.

Preparation Example 1: Preparation of Di(2-Ethylhexyl)

(N,N-dihexylamino)methylphosphonate

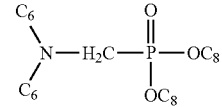

Into a three-necked flask equipped with a mechanical stirrer, a water segregator and a condenser, di(2-ethylhexyl) phosphorite (1 mol), paraformaldehyde (M=30, 1.05 mol), di(n-hexyl)amine (1.05 mol), toluene (700 ml) and p-methylbenzenesulfonic acid (2 g) were added, heated and refluxed at 130° C., and the water produced during reaction was removed. The reaction was performed for another 2 h after no water was produced. The reaction mixture was added with 10 g of potassium carbonate, heated and refluxed for another 15 min, filtered to remove excess potassium carbonate, washed three times with distilled water, and rotarily evaporated to remove toluene to give the targeted product.

$^1$H NMR (400 MHz, CDCl$_3$, ppm): δ 1.74-0.86[m, (CH$_3$)$_6$, (CH$_2$)$_{16}$, (CH)$_2$], 2.63 [m, (CH$_2$)], 2.95[t, CH$_2$, J=8 Hz], 3.96[m, (CH$_2$)$_2$].

Preparation Example 2: Preparation of Dioctyl (N,N-Diisobutylamino)Methylphosphonate

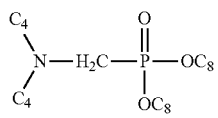

The targeted product was prepared in the same process as that in Preparation Example 1, except that di(n-octyl)phosphorite was used to replace di(2-ethylhexyl)phosphorite, and diisobutylamine was used to replace di(n-hexyl)amine.

$^1$H NMR (400 MHz, CDCl$_3$, ppm): δ 1.71-0.89[m, (CH$_3$)$_6$, (CH$_2$)$_{12}$], 2.05[m, (CH)$_2$], 2.31[m, (CH$_2$)$_2$], 2.95[m, (CH$_2$)], 4.02[m, (CH$_2$)$_2$].

Preparation Example 3: Preparation of Di(2-Ethylhexyl) (Butylamino)Methylphosphonate

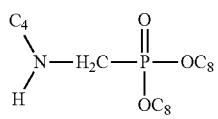

The targeted product was prepared in the same process as that in Preparation Example 1, except that n-butylamine was used to replace di(n-hexyl)amine.

$^1$H NMR (400 MHz, CDCl$_3$, ppm): δ 0.87-1.69 [m, (CH$_3$)$_3$, (CH$_2$)$_6$, NH], 3.14[t, (CH$_2$), J=8 Hz], 3.43[m, (CH$_2$)], 4.02[m, (CH$_2$)$_2$].

Preparation Example 4: Preparation of Di(2-Ethylhexyl) (2-Ethylhexyl)Aminomethyl Phosphonate

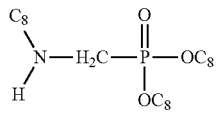

The targeted product was prepared in the same process as that in Preparation Example 1, except that isooctylamine was used to replace di(n-hexyl)amine.

$^1$H NMR (400 MHz, CDCl$_3$, ppm): δ 0.88-1.56[m, (CH$_3$)$_6$, (CH$_2$)$_{12}$, (CH)$_3$, NH], 2.74[d, (CH$_2$), J=4 Hz], 3.14[d, (CH$_2$), J=12 Hz], 3.99[m, (CH$_2$)$_2$].

Preparation Example 5: Preparation of Di(2-Ethylhexyl) (dodecylamino)methylphosphonate

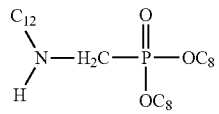

The targeted product was prepared in the same process as that in Preparation Example 1, except that dodecylamine was used to replace di(n-hexyl)amine.

$^1$H NMR (400 MHz, CDCl$_3$, ppm): δ 1.68-0.87[m, (CH$_3$)$_5$, (CH$_2$)$_{18}$, (CH)$_2$, NH], 2.83[t, (CH$_2$), J=7.6 Hz], 3.15[d, (CH$_2$), J=12 Hz], 3.98[m, (CH$_2$)$_2$].

Preparation Example 6: Preparation of Dihexyl (2-Ethylhexyl)Aminomethylphosphonate

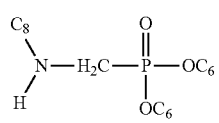

The targeted product was prepared in the same process as that in Preparation Example 4, except that dihexylphosphorite was used to replace di(2-ethylhexyl) phosphorite.

$^1$H NMR (400 MHz, CDCl$_3$, ppm): δ 0.87-1.73[m, (CH$_3$)$_4$, (CH$_2$)$_{12}$, (CH), NH], 2.68[br, (CH$_2$)], 3.14[d, (CH$_2$), J=12 Hz], 3.99[m, (CH$_2$)$_2$].

Preparation Example 7: Preparation of Diheptyl (N,N-Dihexylamino)Methylphosphonate

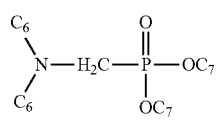

The targeted product was prepared in the same process as that in Preparation Example 1, except that di(n-heptyl) phosphorite was used to replace di(2-ethylhexyl) phosphorite.

$^1$H NMR (400 MHz, CDCl$_3$, ppm): δ 0.88-1.73[m, (CH$_3$)$_4$, (CH$_2$)$_{18}$], 2.48[br, (CH$_2$)$_2$], 2.95[t, CH$_2$, J=8 Hz], 4.02[m, CH$_2$].

Preparation Example 8: Preparation of Di(2-Ethylhexyl) (N,N-dimethylamino)ethylphosphonate

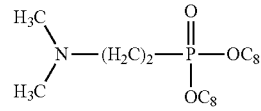

1,2-dibromoethane (0.3 mol) was added into a three-necked flask, heated to 100° C., slowly and dropwisely added with diisooctyl phosphorite, refluxed at 110° C. for 9 h, and distilled under reduced pressure at 110° C. to give diisooctyl 2-bromoethylphosphorite.

The diisooctyl 2-bromoethyl phosphorite obtained above and sodium iodide (5 g) were dissolved in acetone in a single-necked flask, added with excessive dimethylamine (about 0.3 mol), heated to 60° C. and reacted for 24 h. The resultant mixture was washed three times with deionized water, and distilled under reduced pressure to give the targeted product.

$^1$H NMR (400 MHz, CDCl$_3$, ppm): δ 0.88-2.30[m, (CH$_3$)$_4$, (CH$_2$)$_8$, (CH)$_2$], 2.54[d, (CH$_2$)$_6$, J=4 Hz], 2.95[t, (CH$_2$), J=8 Hz)], 3.96[m, (CH$_2$)$_4$].

Example 1

Preparation of organic phase: 3 L of di(2-ethylhexyl) (2-ethylhexyl)aminomethyl phosphonate and 7 L of aviation kerosene were mixed to prepare the organic phase.

The feed solution was a 1.0 mol/L thorium nitrate solution having 3 mol/L nitric acid.

The scrubbing solution was a 3.0 mol/L nitric acid solution.

The stripping agent was a 0.1 mol/L nitric acid solution.

The extraction and separation experiment was performed in 250 ml mixer-settler extractors. Firstly, 5 stages of counter-current extraction were performed to give a thorium-loaded organic phase and a raffinate, wherein the flow ratio of the organic phase and the feed solution was 16 mL/min: 4 mL/min. Then, 3 stages of counter-current washing were performed, wherein the flow ratio of the thorium-loaded organic phase and the scrubbing solution was 16 mL/min: 4 mL/min. Next, 4 stages of counter-current back-extraction was performed to give a thorium-containing stripping solution, wherein the flow ratio of the thorium-loaded organic phase and the stripping agent was 16 mL/min: 16 mL/min. The obtained stripping solution was precipitated by oxalic acid, and the precipitate was filtered, washed, dried, and sintered to give thorium oxide with a purity of 99.99%, calculated based on thorium dioxide.

Example 2

Preparation of organic phase: 2 L of di(2-ethylhexyl) (N,N-hexylamino)methylphosphonate, 1 L of di(2-ethylhexyl) 2-ethylhexylphosphonate, 1 L of 2-methyl heptanol and 6 L of aviation kerosene were mixed to prepare the organic phase.

The feed solution was a 0.30 mol/L thorium nitrate solution having an acidity of 2.0 mol/L.

The scrubbing solution was a 2.0 mol/L nitric acid solution.

The stripping agent was a 0.5 mol/L nitric acid solution.

The extraction and separation experiment was performed in centrifugal extractors. Firstly, 3 stages of countercurrent extraction was performed to give a thorium-loaded organic phase and a raffinate, wherein the flow ratio of the organic phase and the feed solution was 10 mL/min: 5 mL/min. Then, 4 stages of countercurrent washing was performed, wherein the flow ratio of the thorium-loaded organic phase and the scrubbing solution was 10 mL/min: 5 mL/min. Next, 5 stages of countercurrent back-extraction was performed to give a thorium-containing stripping solution, wherein the flow ratio of the thorium-loaded organic phase and the stripping agent was 10 mL/min: 2.5 mL/min. The obtained stripping solution was precipitated by oxalic acid, and the precipitate was filtered, washed, dried, and sintered to give thorium oxide with a purity of 99.99%, calculated based on thorium dioxide.

Example 3

Preparation of organic phase: 3 L of dioctyl (N,N-diisobutylamino)methylphosphonate, 1 L of TBP and 6 L of aviation kerosene were mixed to prepare the organic phase.

The feed solution was a 1.5 mol/L thorium nitrate solution having an acidity of 2.0 mol/L.

The scrubbing solution was a 1.0 mol/L nitric acid solution.

The stripping agent was a 4 mol/L hydrochloric acid solution.

The extraction and separation experiment was performed in 250 ml mixer-settler extractors. Firstly, 5 stages of countercurrent extraction was performed to give a thorium-loaded organic phase and a raffinate, wherein the flow ratio of the organic phase and the feed solution was 17 mL/min: 2 mL/min. Then, 4 stages of countercurrent washing was performed, wherein the flow ratio of the thorium-loaded organic phase and the scrubbing solution was 17 mL/min: 6 mL/min. Next, 5 stages of countercurrent back-extraction was performed to give a thorium-containing stripping solution, wherein the flow ratio of the thorium-loaded organic phase and the stripping agent was 17 mL/min: 5 mL/min. The obtained stripping solution was precipitated by oxalic acid, and the precipitate was filtered, washed, dried, and sintered to give thorium oxide with a purity of 99.95%, calculated based on thorium dioxide.

Example 4

Preparation of organic phase: 0.5 L of di(2-ethylhexyl) (butylamino)methylphosphonate and 9.5 L of heptane were mixed to prepare organic phase.

Feed solution was 0.001 mol/L of thorium sulfate containing 0.5 mol/L of sulphuric acid, 0.06 mol/L of phosphoric acid, and 0.05 mol/L of hydrofluoric acid.

Scrubbing solution was 0.3 mol/L of sulphuric acid solution.

Stripping agent was 1% sodium carbonate solution.

The extraction and separation experiment was performed in 250 ml mixer-settler extractors. Firstly, 10 stages of countercurrent extraction was performed to give a thorium-loaded organic phase and a raffinate, wherein the flow ratio of the organic phase and the feed solution was 2 mL/min: 20 mL/min. Then 4 stages of counter current washing was performed, wherein the flow ratio of the thorium-loaded organic phase and the scrubbing solution was 2 mL/min: 2 mL/min. Next, 5 stages of counter current back-extraction was performed to give a thorium-containing stripping solution, wherein the flow ratio of the thorium-loaded organic phase and the stripping agent was 2 mL/min: 1 mL/min. The obtained stripping solution was precipitated by oxalic acid, and the precipitate was filtered, washed, dried, and sintered to give thorium oxide with a purity of 99.95%, calculated based on thorium dioxide.

Example 5

Preparation of organic phase: 2.5 L of di(2-ethylhexyl) (dodecylamino)methylphosphonate, 0.5 L of Cyanex 923 and 7 L of xylene were mixed to prepare the organic phase.

The feed solution was a 0.03 mol/L thorium sulfate solution having an acidity of 0.5 mol/L.

The stripping agent was a 2% sodium carbonate solution.

The extraction and separation experiment was performed in 250 ml mixer-settler extractors. Firstly, 10 stages of countercurrent extraction was performed to give a thorium-loaded organic phase and a raffinate, wherein the flow ratio of the organic phase and the feed solution was 3 mL/min: 18 mL/min. Next, 5 stages of countercurrent back-extraction was performed to give a thorium-containing stripping solution, wherein the flow ratio of the thorium-loaded organic phase and the stripping agent was 3 mL/min: 2 mL/min. The obtained stripping solution was precipitated by oxalic acid, and the precipitate was filtered, washed, dried, and sintered to give thorium oxide with a purity of 99.8%, calculated based on thorium dioxide.

Example 6

Preparation of organic phase: 0.5 L of diheptyl (N,N-dihexylamino)methylphosphonate and 9.5 L of heptane were mixed to prepare the organic phase.

The feed solution was a 0.001 mol/L thorium nitrate solution with a nitric acid concentration of 1 mol/L.

The scrubbing solution was a 1 mol/L nitric acid solution.

The stripping agent was a 0.2 mol/L nitric acid solution.

The extraction and separation experiment was performed in centrifugal extractors. Firstly, 10 stages of countercurrent extraction was performed to give a thorium-loaded organic phase and a raffinate, wherein the flow ratio of the organic phase and the feed solution was 2 mL/min: 20 mL/min. Then, 4 stages of countercurrent washing was performed, wherein the flow ratio of the thorium-loaded organic phase and the scrubbing solution was 2 mL/min: 2 mL/min. Next, 5 stages of countercurrent back-extraction was performed to give a thorium-containing stripping solution, wherein the flow ratio of the thorium-loaded organic phase and the stripping agent was 2 mL/min: 2 mL/min. The obtained stripping solution was precipitated by oxalic acid, and the precipitate was filtered, washed, dried, and sintered to give thorium oxide with a purity of 99.9%, calculated based on thorium dioxide.

Example 7

Preparation of organic phase: 3 L of dihexyl (2-ethylhexyl)aminomethylphosphonate, 1 L of 2-methyl heptanol and 6 L of aviation kerosene were mixed to prepare the organic phase.

The feed solution was a 0.30 mol/L thorium hydrochloride solution with a hydrochloric acid concentration of 0.3 mol/L.

The scrubbing solution was a 0.3 mol/L hydrochloric acid solution.

The stripping agent was a 2 mol/L sulfuric acid solution.

The extraction and separation experiment was performed in 250 ml mixer-settler extractors. Firstly, 3 stages of countercurrent extraction was performed to give a thorium-loaded organic phase and a raffinate, wherein the flow ratio of the organic phase and the feed solution was 10 mL/min: 5 mL/min. Then, 4 stages of countercurrent washing was performed, wherein the flow ratio of the thorium-loaded organic phase and the scrubbing solution was 10 mL/min: 5 mL/min. Next, 5 stages of countercurrent back-extraction was performed to give a thorium-containing stripping solution, wherein the flow ratio of the thorium-loaded organic phase and the stripping agent was 10 mL/min: 6 mL/min. The obtained stripping solution was precipitated by oxalic acid, and the precipitate was filtered, washed, dried, and sintered to give thorium oxide with a purity of 99.95%, calculated based on thorium dioxide.

Example 8

The operation and equipment were the same as those in Example 1, except that di(2-ethylhexyl) (N,N-dimethylamino)ethylphosphonate was used as the extractant instead of di(2-ethylhexyl) (2-ethylhexyl)aminomethylphosphonate. The purity of thorium is 99.9%, calculated based on thorium dioxide.

Example 9

1. Preparation of Extraction Resin 50 mL of di(2-ethylhexyl) (2-ethylhexyl)aminomethylphosphonate and 50 mL of a mixture of styrene and divinyl benzene were mixed to prepare an oil phase, wherein the volume ratio of styrene and divinyl-benzene was 2:1.1.5 g of gelatin, 2.5 g of ammonium thiocyanate were added to 500 mL of deionized water, and heated to 50° C. After the gelatin was completely dissolved, the oil phase was slowly added thereto, and the mixture was stirred for half an hour, heated to 80° C. to react for 5 h, and then heated to 90° C. to cure for half an hour. The resin was filtered, washed with water and air dried to give 75 g of extracting resin.

2. Extraction Experiment 50 g of extraction resin was filled into a separation column, and a thorium-containing feed solution, which is a 0.10 mol/L thorium nitrate solution with an acidity of 3 mol/L, was introduced with a flow rate of 2 mL/min. The eluate was sampled and measured every 5 min. The introduction of feed solution was stopped when the thorium content in the raffinate was larger than 0.01 g/L. A scrubbing solution, which is a 3 mol/L nitric acid solution, was introduced with a flow rate of 2 mL/min to wash the thorium-loaded extraction resin. The introduction of the scrubbing solution was stopped when the thorium content in eluate was less than 0.1 g/L. A stripping agent, which is a 0.2 mol/L nitric acid solution, was introduced with a flow rate of 2 mL/min. When the thorium concentration in the eluate is less than 0.01 g/L, the back-extraction was completed to give a thorium-containing stripping solution. The pH of the obtained stripping solution was adjusted, and then added with oxalic acid to precipitate thorium. The precipitate was filtered, washed, dried, and sintered to give a thorium oxide solid with a yield of 91%, and a purity of 99.999%, calculated based on thorium dioxide.

The invention claimed is:

1. A process of extracting thorium, comprising a step of extracting thorium by solvent extraction or solid-liquid extraction using the amino-containing neutral phosphine extractant of Formula I

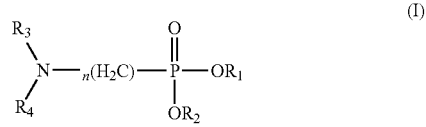

wherein,
$R_1$ and $R_2$ are each independently selected from the group consisting of $C_1$-$C_{12}$ alkyl;
$R_3$ and $R_4$ are each independently selected from the group consisting of $C_1$-$C_{16}$ alkyl and hydrogen; and n is an integer of 1 to 8,
wherein the solvent extraction comprises: mixing a neutral phosphine extraction system including the amino-containing neutral phosphine extractant of Formula I and a thorium-containing feed solution to form a thorium-loaded organic phase and a raffinate;
wherein the solid-liquid extraction comprises: contacting a solid separation material containing the amino-containing neutral phosphine extractant of Formula I with a thorium-containing feed solution to form a thorium-containing solid separation material and a raffinate.

2. The process according to claim 1, wherein the sum of carbon atoms in $R_1$ and $R_2$ is an integer of 8 to 20.

3. The process according to claim 1, wherein $R_3$ is selected from the group consisting of $C_1$-$C_{10}$ alkyl and hydrogen; and
$R_4$ is selected from $C_1$-$C_{14}$ alkyl.

4. The process according to claim 1, wherein $R_1$ and $R_2$ are each independently selected from the group consisting of $C_4$-$C_{10}$ alkyl.

5. The process according to claim 1, wherein $R_1$ and $R_2$ are the same alkyl.

6. The process according to claim 1, wherein the sum of the total carbon atoms in $R_3$ and $R_4$ is an integer of 1 to 16.

7. The process according to claim 1, wherein the sum of the carbon atoms of $R_1$, $R_2$, $R_3$, $R_4$ and —$(CH_2)_n$— is 14 to 36.

8. The process according to claim 1, wherein the amino-containing neutral phosphine extractant of Formula I is one or more selected from the group consisting of di(2-ethylhexyl) (2-thylhexyl)aminomethylphosphonate, di(2-ethylhexyl) hexylaminomethylphosphonate, di(2-ethylhexyl) (N,N-diisobutylamino)methylphosphonate, di(2-ethylhexyl) butylaminomethylphosphonate, and dihexyl dodecylaminomethylphosphonate.

9. The process according to claim 1, wherein,
the neutral phosphine extraction system includes the amino-containing neutral phosphine extractant of formula I, an optional auxiliary extractant, an optional phase modifier and a diluent; and
the solid separation material containing the neutral phosphine extractant of Formula I is a resin, porous silica beads or diatomaceous earth loaded with the neutral phosphine extractant of Formula I.

10. The process according to claim 9, wherein,
the volume ratio of the amino-containing neutral phosphine extractant of Formula I, the auxiliary extractant, the phase modifier and the diluent is: the amino-containing neutral phosphine extractant:the auxiliary extractant:the phase modifier:the diluent=1-60:0-40:0-20:40-110; and
the solid separation material containing the neutral phosphine extractant of Formula I is an extracting resin.

11. The process according to claim 9, wherein,
the auxiliary extractant is selected from the group consisting of phosphorus or phosphine extractant of Formula VII:

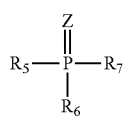

(VII)

wherein,
Z is O or S;
$R_5$ is selected from the group consisting of hydrogen, $C_1$-$C_{12}$ alkyl, $C_1$-$C_{12}$ alkoxy, —SH, and —$NH_2$ substituted by at least one substituent selected from the group consisting of $C_1$-$C_{12}$ alkyl;

$R_6$ and $R_7$ are each independently selected from the group consisting of $C_4$-$C_{12}$ alkyl, $C_4$-$C_{12}$ alkoxy, and —$NH_2$ substituted with at least one substituent selected from the group consisting of $C_4$-$C_{12}$ alkyl;
the phase modifier is one or more selected from the group consisting of $C_4$-$C_{10}$ alkanol; and
the diluent is one or more selected from the group consisting of $C_5$-$C_{16}$ alkane, aviation kerosene, sulfonated kerosene, liquid paraffin, $C_5$-$C_{16}$ alicyclic hydrocarbon, and $C_6$-$C_{10}$ aromatic hydrocarbon.

12. The process according to claim 11, wherein,
the auxiliary extractant is selected from the group consisting of tri(linear alkyl)phosphine oxide, tri(branched alkyl)phosphine oxide, trioctylphosphine oxide, di(m-ethylheptyl) methylphosphonate, di(2-ethylhexyl)-2-ethylhexylphosphonate, tributyl phosphate, bis(2,4,4-trimethylpentyl)dithiophosphinic acid, bis(2,4,4-trimethylpentyl)monithiophosphinic acid, di(2-ethylhexyl)phosphoric acid, mono(2-ethylhexyl) 2-ethylhexylphosphonate, bis(2,4,4-trimethylpentyl) phosphinic acid, bis(2-ethylhexyl)phosphonic acid, tri-isooctylphosphamide, bisisooctyl-isooctoxyphosphamide, isooctyl bisisooctoxyphosphamide, tri(bisisobutyl)phosphamide, bis(bisisobutyl) isooctoxyphosphoramide, tridecylphosphamide, bishexyl decyloxyphosphamide and a mixed extractant thereof in any ratio;
the phase modifier is one or more selected from n-octanol, isooctanol, 2-methyl heptanol or a mixed alcohol thereof in any ratio; and
the diluent is one or more selected from the group consisting of aviation kerosene, sulfonated kerosene, heptane and xylene.

13. The process according to claim 1, wherein,
in the extraction step of the solvent extraction, the number of the extraction stages is 1 to 10; and the flow ratio of the neutral phosphine extraction system and the feed solution is 0.1-20:1.

14. The process according to claim 1, wherein,
the solvent extraction further includes an optional step of washing the thorium-loaded organic phase using a scrubbing solution, and a step of back-extracting the thorium in the thorium-loaded organic phase using a stripping agent to give a thorium-containing stripping solution; and
the solid-liquid extraction further comprises an optional step of washing the thorium-containing solid separation material using a scrubbing solution, and a step of back-extracting the thorium in the thorium-containing solid separation material using a stripping agent.

15. The process according to claim 14, wherein,
the scrubbing solution is a solution of nitric acid, sulfuric acid, hydrochloric acid, or a mixture thereof in any ratio; and
the stripping agent is a solution of nitric acid, hydrochloric acid, sulfuric acid, a mixture thereof, or a carbonate aqueous solution.

16. The process according to claim 15, wherein,
the acidity of the scrubbing solution, calculated in molar concentration of the hydrogen ion, is 0.2 to 8 mol/L;
in the case of using an acid solution as the stripping agent, the acidity of the stripping agent, calculated in molar concentration of the hydrogen ion, is 0.05 to 2 mol/L; and
in the case of using a sodium carbonate aqueous solution as the stripping agent, the concentration of sodium carbonate in the solution is 0.5 to 5 wt %.

17. The process according to claim 15, wherein, the stripping agent is a diluted nitric acid solution with a concentration of 0.1 to 0.5 mol/L or a sodium carbonate aqueous solution with a concentration of 0.5 to 3 wt %.

18. The process according to claim 14, wherein, in the solvent extraction, the number of the washing stages is 0 to 10; and the flow ratio of the thorium-loaded organic phase and the scrubbing solution is 1-0.1:2;

in the solvent extraction, the number of the back-extracting stages is 1 to 10; and the flow ratio of the thorium-loaded organic phase and the stripping agent is 1:0.1-10.

19. The process according to claim 14, wherein, in the solvent extraction, the extracting, washing and back-extracting are performed in a series of separatory funnels, mixer-settler extractors or centrifugal extractors; and in the solvent extraction, the extracting, washing and back-extraction are performed in batches or continuously.

* * * * *